US011266279B2

(12) United States Patent
Glenn

(10) Patent No.: US 11,266,279 B2
(45) Date of Patent: Mar. 8, 2022

(54) TOILET SEAT SANITIZER

(71) Applicant: Stephen Glenn, Bentonville, AR (US)

(72) Inventor: Stephen Glenn, Bentonville, AR (US)

( * ) Notice: Subject to any disclaimer, the term of this patent is extended or adjusted under 35 U.S.C. 154(b) by 22 days.

(21) Appl. No.: 15/931,997

(22) Filed: May 14, 2020

(65) Prior Publication Data

US 2020/0359856 A1    Nov. 19, 2020

Related U.S. Application Data

(60) Provisional application No. 62/848,225, filed on May 15, 2019.

(51) Int. Cl.
| | | |
|---|---|---|
| *A47K 13/30* | (2006.01) | |
| *A61L 2/08* | (2006.01) | |
| *A47K 17/00* | (2006.01) | |

(52) U.S. Cl.
CPC ............ *A47K 13/302* (2013.01); *A47K 17/00* (2013.01); *A61L 2/084* (2013.01)

(58) Field of Classification Search
CPC .............................. A47K 13/302; A47K 17/00
See application file for complete search history.

(56) References Cited

U.S. PATENT DOCUMENTS

| | | | | |
|---|---|---|---|---|
| 5,123,124 A | * | 6/1992 | Brower | A47K 13/10 |
| | | | | 4/217 |
| 5,564,134 A | * | 10/1996 | Ruth | A47K 13/302 |
| | | | | 222/181.2 |
| 6,467,651 B1 | * | 10/2002 | Muderlak | A47K 5/1217 |
| | | | | 222/333 |
| 2002/0100771 A1 | * | 8/2002 | Redman | A47K 5/1204 |
| | | | | 222/255 |
| 2007/0256226 A1 | * | 11/2007 | Pinizzotto | E03D 9/08 |
| | | | | 4/420.4 |
| 2008/0028506 A1 | * | 2/2008 | DiPano | A47K 13/302 |
| | | | | 4/233 |
| 2010/0071121 A1 | * | 3/2010 | Kissner | E03D 9/032 |
| | | | | 4/223 |
| 2017/0058500 A1 | * | 3/2017 | Garrels | E03D 1/36 |
| 2018/0235416 A1 | * | 8/2018 | Poleki | A47K 13/302 |
| 2019/0063054 A1 | * | 2/2019 | Luettgen | E03D 9/033 |

* cited by examiner

*Primary Examiner* — J C Jacyna
(74) *Attorney, Agent, or Firm* — Jeff Cameron; Michael Cameron

(57) ABSTRACT

An apparatus for cleaning and sanitizing toilet seats, bowls, rims and related appurtenances. It comprises a solution reservoir, an articulable dispensing nozzle, and a push-button or activation mechanism which, when pressed or activated, sprays a desired surface with cleaning solution. The apparatus is operable to permit quick consistent cleaning of toilet seats and other surfaces and is easily attached to a wide variety of existing toilets.

10 Claims, 7 Drawing Sheets

TOILET SEAT SANITIZER

CROSS REFERENCE TO RELATED APPLICATION

This application claims priority to U.S. Ser. No. 62/848,225, filed May 15, 2019 entitled: TOILET SEAT SANITIZER, the contents of which are incorporated herein by reference.

TECHNICAL FIELD

The present invention relates to cleaning equipment used to sanitize toilet seats, bowls.

BACKGROUND

Public toilets see frequent use and must be regularly sanitized for health and aesthetic reasons, a process which can require significant man-hours, either by janitorial staff of other employees. If a toilet is not clean, patrons must ask employees for assistance as public restrooms are often not stocked with the cleaning supplies necessary for patrons to sanitize a toilet themselves due to safety or theft concerns, nor are users of public toilets usually willing to devote the required effort. This can lead to awkward situations and unhappy employees and users. Many of these concerns also apply to residential toilets, especially those which see frequent use by multiple people—those in dormitories or homes having large families, for example.

In a recent study, it has been determined that Coronavirus, the virus responsible for COVID-19, can be spread through a "toilet plume" after a toilet is flushed by an infected person, a study suggests. Researchers with the American Journal of Infection Control say the disease can be spread through fecal matter that escapes the toilet bowl during a flush. Research indicates that fecal matter can be propelled into the air in a toilet plume. The plume could play a contributory role in the transmission of infectious diseases. "Potentially infectious aerosols may be produced in substantial quantities during flushing," researchers wrote, "Aerosolization can continue through multiple flushes to expose subsequent toilet users."

While closing the lid of the toilet before flushing can prevent the spread of the coronavirus, according to the American Journal of Infection Control, extra precautions such as sanitizing the toilet bowl may help stop the spread of the Coronavirus.

UV-A light, commonly referred to as blacklight, refers to a long-wave type of ultraviolet (UV) light which is particularly useful in observing fluorescence, the phenomenon in which certain materials or substances absorb and then re-emit light. When the absorbed light is a non-visible wavelength like ultraviolet and the emitted light in the visible range, a substance will appear to glow. Sources of blacklight can include lamps, lasers or some light-emitting diodes (LEDs). Human and animal waste products such as urine are among the substances that fluoresce in response to UV light.

What is desired is a standardized apparatus which can be retrofitted to a wide variety of toilets and which allows for quick, easy, and consistent sanitization of the toilet seat, bowl, rim and related appurtenances.

SUMMARY

The present invention comprises a sanitization apparatus having a reservoir which holds a cleaning or sanitizing solution, a dispensing nozzle (in an embodiment, hinged or articulable, and another embodiment, fixed and/or telescoping), an activating mechanism being manual push button or sensor driven, a conduit between the reservoir and nozzle and a mechanism for attaching to a toilet or to a surface in close proximity to a toilet. The nozzle may be adjusted and/or aimed for consistent coverage of the desired surface for ease of use and reliability. Such adjustment can be from a stream to a flat, round or oval spray. Once said surface is sufficiently covered, a user can then wipe said surface with toilet paper or paper towels which can then be easily disposed in a trashcan or the toilet itself.

In the preferred embodiment the dispensing nozzle is a movable, or articulable spray-nozzle which can be positioned or aimed and its spread adjusted such that when it is activated, said nozzle dispenses a layer of solution onto the desired surface, be it the toilet seat, rim, bowl, etc. In the preferred embodiment said activating mechanism is a simple push-button which uses the force of a user's push to mechanically move solution from said reservoir through a one-way valve mid through said nozzle which breaks up the liquid solution into a fine mist or aerosol and distributes it evenly on to a desired surface. A user then wipes down said surface with, for example, toilet paper. In an embodiment, the liquid is self-drying, having a content of at least sixty percent (60%) isopropyl alcohol. This apparatus thus provides a consistent, precise, fast, low-effort way to clean and/or sanitize surfaces. The invention further comprises a user-activated or automatically sensing UV light for the illumination of urine and other matter on the surfaces to be cleaned.

To those skilled in the art to which this invention relates, many changes in construction and widely differing embodiments and applications of the invention will suggest themselves without departing from the scope of the invention as defined herein. The disclosures and the descriptions herein are purely illustrative and are not intended to be in any sense limiting.

BRIEF DESCRIPTION OF THE DRAWINGS

For a better understanding of the present invention including the features, advantages and embodiments, reference is made to the following detailed description along with accompanying Figures which show one embodiment of the present invention in several mounting configurations.

DETAILED DESCRIPTION

While the making and using of the disclosed embodiments of the present invention is discussed in detail below, it should be appealed that the present invention provides many applicable inventive concepts which can be embodied in a wide variety of contexts. Some features of the preferred embodiments shown and discussed may be simplified or exaggerated for illustrating the principles of the invention.

Figure 1:
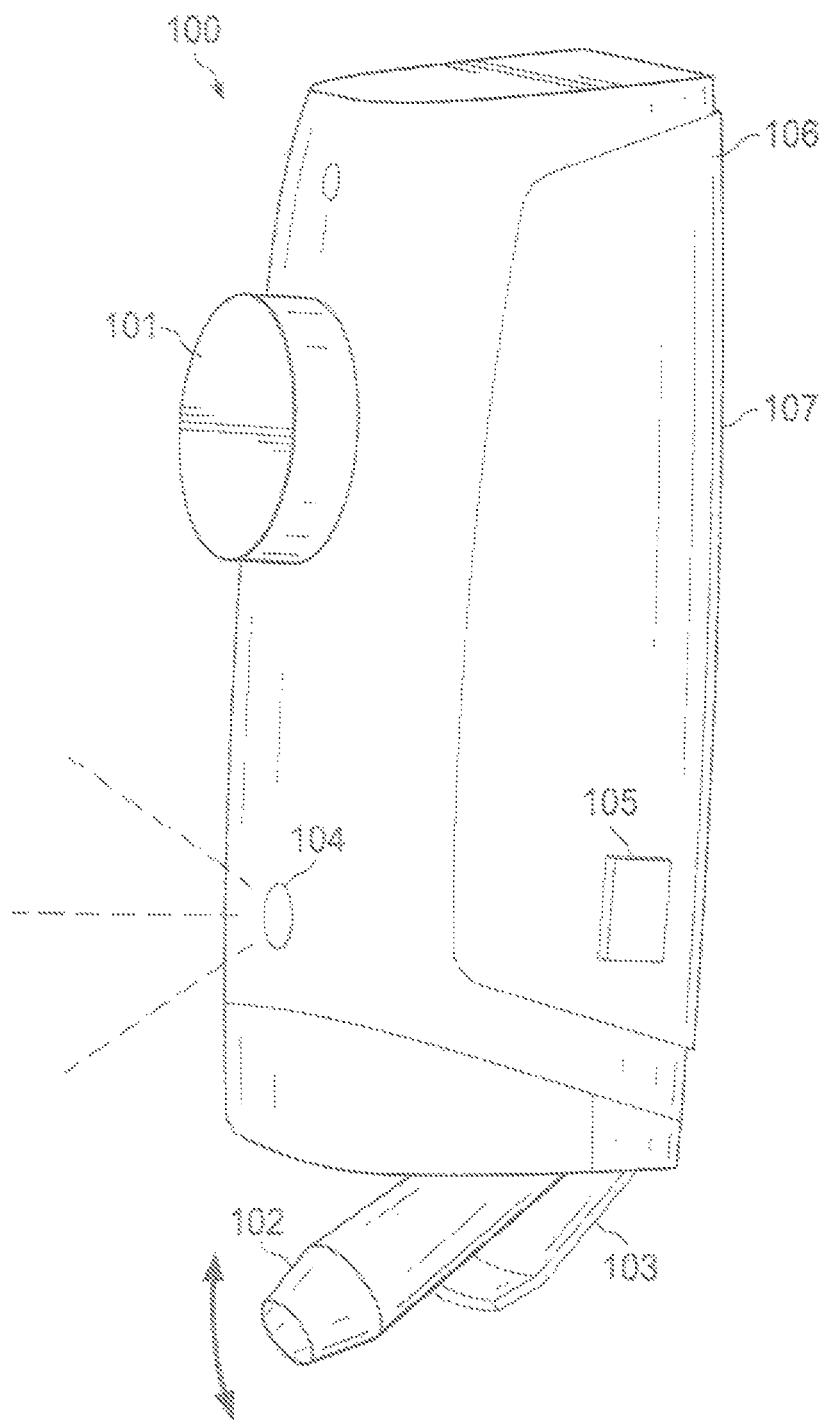
FIG. 1 shows a perspective view of one embodiment of the present invention.

Referring to FIG. 1, the present invention comprises a sanitization apparatus 100 having a housing 106, a reservoir internal to said housing, said reservoir containing a cleaning or sanitizing solution, a dispensing nozzle 102, an aiming mechanism 103 for said nozzle, an activating mechanism 101, a conduit from the reservoir to the nozzle and an attachment mechanism 107 for attaching to a toilet or to a surface in close proximity to a toilet.

In the preferred embodiment the dispensing nozzle 102 is an articulable spray-nozzle which can be positioned or aimed via a hinge, ball-joint, or other aiming mechanism 103 and its spread adjusted such that when it is activated, said nozzle dispenses a layer of solution onto the desired surface, be it the toilet seat, rim, bowl, and related appurtenances, said solution being in one embodiment a low-residue sanitizer such as isopropyl alcohol, said dispensing nozzle being coupled to the an articulation joint 103 such as a ball-and-socket joint (a ball-and-socket or ball joint being a mechanical joint which allows for free rotation in two planes simultaneously while preventing translation in any direction) or hinge joint, (a hinge, pin or revolute joint being a mechanical joint allowing for rotation about a single axis), allowing for the adjustment and maintenance within a range of angles of the lateral and/or longitudinal location of an aiming point by a user, or any articulation mechanism which allows for the adjustment of the yaw and/or pitch, i.e. the lateral and/or devotional aiming, of said nozzle with respect to a toilet; said nozzle further comprising a mechanism for adjusting the spread of resulting spray, said spread adjustment mechanism comprising in a preferred embodiment a screw joint, said screw joint being a simple mechanism comprising two coaxial, complementary pieces, one inside the other, the outer surface of said inner piece and the inner surface of said outer piece being threaded such that rotation of one with respect to the other causes longitudinal movement of one with respect to the other, said liquid solution being forced from said reservoir by a pressure differential through a channel or conduit running axially through said inner piece until it impacts a spreader and is redirected partially laterally outward from said channel through openings in said outer piece, the twisting of said outer piece with respect to said inner piece being operable to change the geometry encountered by said solution and thus change the spread of said resulting spray.

In the preferred embodiment said activating mechanism 101 is a simple push-button which acts as a positive-displacement pump, a user's push being operable to pressurize said reservoir, forcing solution from said reservoir through a one-way valve and toward said nozzle 102 which breaks up the liquid solution into a fine mist. Said push-button must necessarily be large enough that the stroke distance sufficiently pressurizes said reservoir to send an effective amount of elation through said nozzle at an effective pressure, an effective amount being an amount that adequately coats a desired surface for sanitization purposes, an effective pressure being a pressure which allows said solution to reach a desired distance from said nozzle in order to sanitize the entire toilet seat, bowl rim, etc. In a further embodiment, the push button is recessed into the reservoir or is positioned on the top of the reservoir so that it is not inadvertently pushed when a person is sitting on the toilet seat. In a further embodiment, the activation of the pump can be via a mechanical motor and sensor assembly powered by a power source such as a battery or low voltage solar panel.

In the preferred embodiment the present invention further comprises a blacklight LED 104, a blacklight activation button 105, and the associated necessary circuitry and power supply including batteries, said blacklight being positioned on said housing 106 such that, when activated, it illuminates substances such as urine, fecal material, etc, on the surfaces which are to be cleaned or sanitized. In another embodiment, the apparatus further comprises a visible-light LED coupled to a motion sensor and power source such that the visible-light LED activates when a user comes into the proximity of the apparatus.

Figure 2:
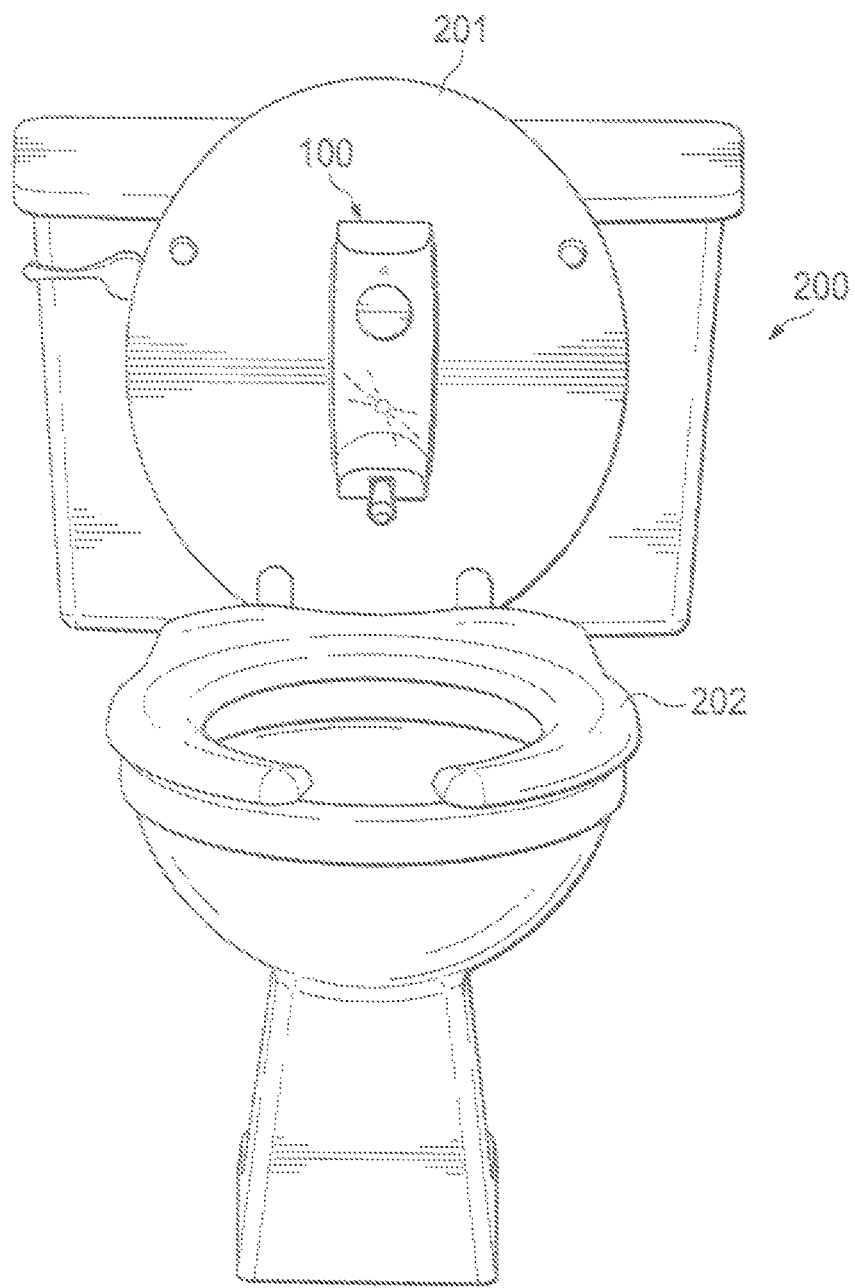
FIG. 2 shows the invention attached to a toilet lid in one embodiment of the present invention.

In a preferred embodiment, and referring to FIG. 2, if the toilet 200 to which said apparatus 100 is to be affixed comprises an upper lid 201, the attachment mechanism 107 is an adhesive such as double-sided tape and the corresponding attachment method consists of securely affixing a mounting bracket to the approximate center of said lid, said apparatus housing 106 comprising on its rear-facing side a corresponding locking insert, said locking insert being inserted into said mounting bracket such that said insert and the attached apparatus may be positioned via sliding by a user along a direction which is defined as upwards or downwards when said toilet lid is in a raised position, the complementary geometry of said mounting bracket and said insert being operable to look said apparatus into position at any of various heights along said mounting bracket, the dimensions of said apparatus when at a stowed position (i.e., when said apparatus is in a neutral, un-extended position with respect to said mounting bracket) being such that when said lid 201 is lowered, or when a secondary seat 202 is raised, said apparatus and mounting bracket fit into the opening in the associated toilet seat, the dimensions of the semi-major and semi-minor diameters of the inner elliptical opening of a standard toilet seat being approximately 9 and ⅞ inches and 8 and ¼ inches respectively, said complementary geometry being in one embodiment a set of corresponding interlocking teeth made of a rigid but flexible material such as a common plastic, one set of teeth comprising a release tab, said tab when depressed being operable to temporarily open or unlock said interlocking teeth via movement of one set of teeth relative to the other by elastic deformation to allow for movement of the apparatus with respect to the mounting bracket, constrained to translation along one axis, said teeth then returning to their interlocked state once said fixture is positioned as desired with respect to said mounting bracket. In another embodiment, said apparatus may exist in a variety of sizes dimensioned to hold larger or smaller amounts of cleaning solution for different purposes, e.g., residential versus commercial uses. For example, the toilet and toilet bowl sanitizing apparatus can be dimensioned between 8 and 11 inches tall and between 6 and 9 inches wide, such that said apparatus fits into the inner opening of a standard toilet seat.

Figure 3:
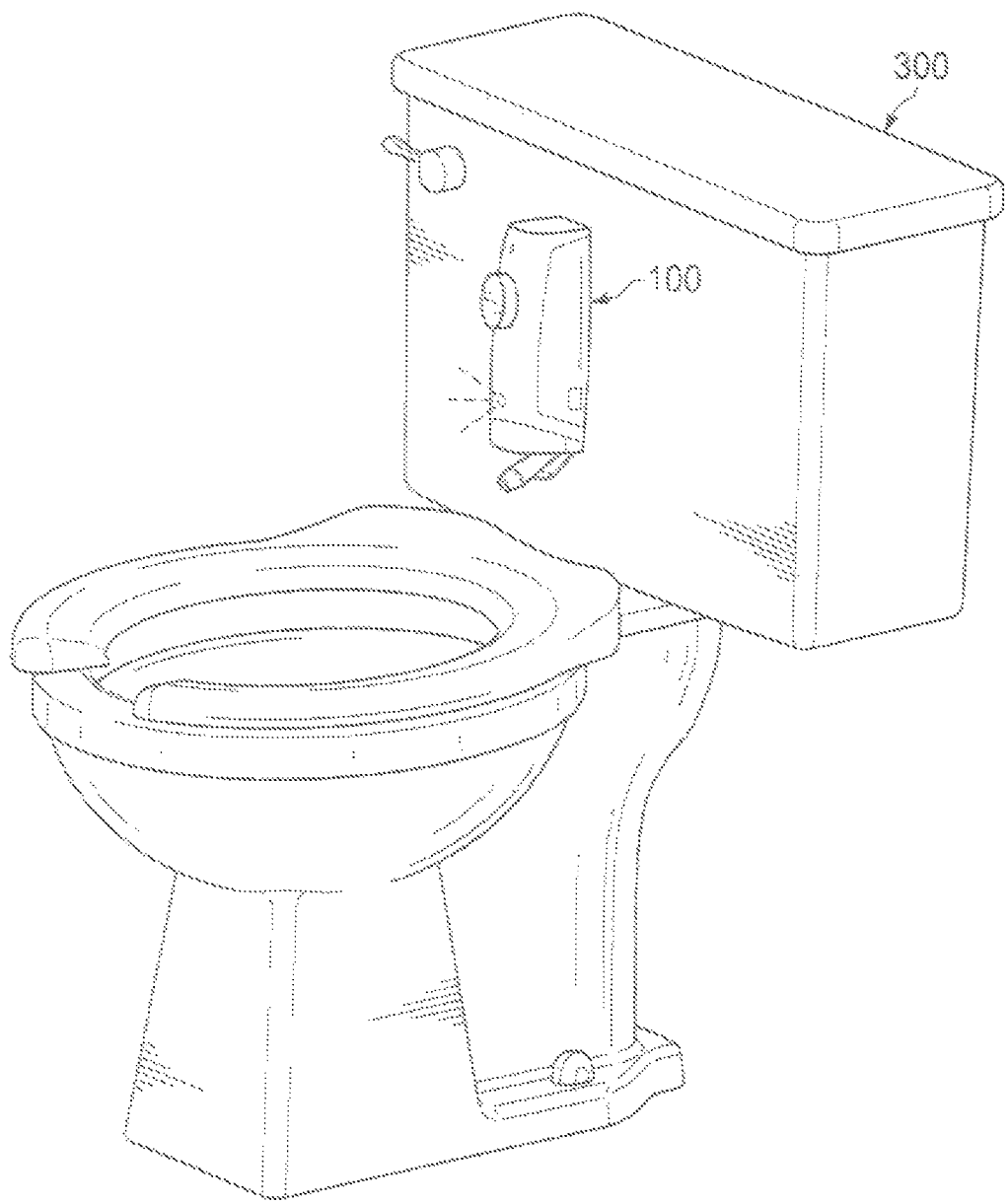
FIG. 3 shows the invention attached to a toilet tank in one embodiment of the present invention.
Figure 4:
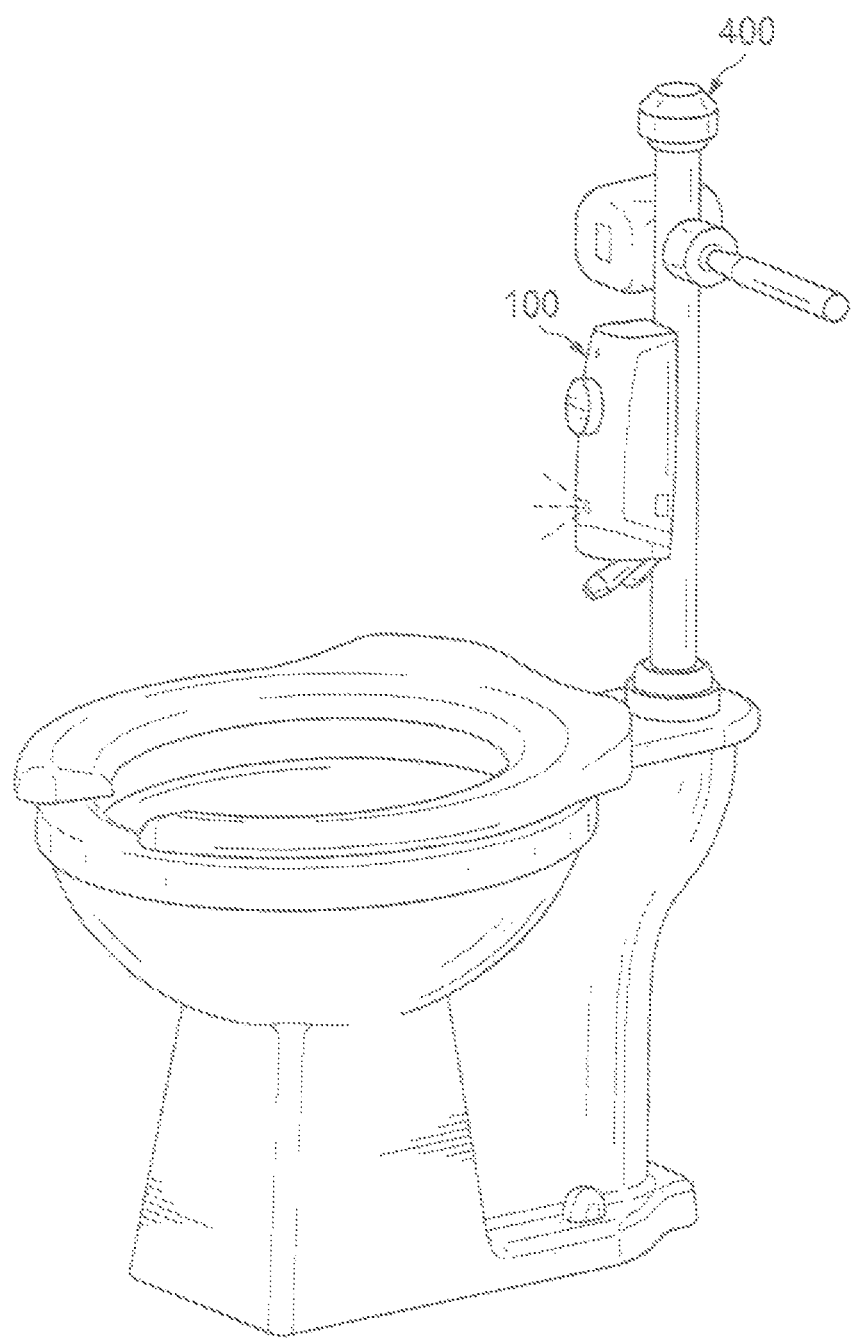
FIG. 4 shows the invention attached to a pipe in one embodiment of the present invention.

Referring to FIG. 3, if said toilet does not comprise an upper lid 201 but does comprise a tank 300, said apparatus and mounting bracket may be similarly affixed to said tank, both attachment methods placing the apparatus slightly above and behind the toilet seat to be sanitized. Referring to FIG. 4, if said toilet does not comprise an upper lid 201 or tank 300 said apparatus may be affixed by cylindrical brackets or adhesive to a suitably-positioned water pipe 400 or by adhesive or wall-mounted bracket to a nearby vertical surface; in one embodiment said attachment mechanism comprise one or more thin-walled cylindrical brackets positioned along a common axis, being attached to said apparatus along a common longitudinal line, being made of a rigid but flexible material such as a common plastic, and having an opening opposite said attachment line, such that said apparatus may be secured to a pipe or other cylindrical fixture, said brackets opening temporarily via elastic deformation to admit said cylindrical fixture and then returning to their original shape once said fixture is aligned axially with said brackets. In another embodiment said apparatus housing comprises on its rear-facing side a high-friction, "no-slip" backing material such as rubber, and said attachment mechanism comprises a simple fastener such as a cable tie or zip tie, said zip tie being used to secure said apparatus against a pipe, said backing material providing sufficient frictional force to maintain a desired position.

In an embodiment, said housing or frame is a thin ovoid comprising openings for said nozzle and said activating mechanism, and a locking, openable section for replacement of said reservoir. In another embodiment, said housing or frame is a rectangular prism comprising openings for said nozzle and said activating mechanism, and a locking, openable section for replacement of said reservoir.

The nozzle, whether fixed, articulable or hinged, has a sufficiently large pump displacement and therefore nozzle range to allow for a large number of effective mounting locations from which a toilet can be reached by said solution spray. Further, the adjustable mounting bracket allows for both precise, consistent targeting of said nozzle and a compact form factor when stowed or placed in a neutral configuration. Said apparatus may also be removed from said mounting bracket, being operable as a portable spray bottle.

Figure 6:
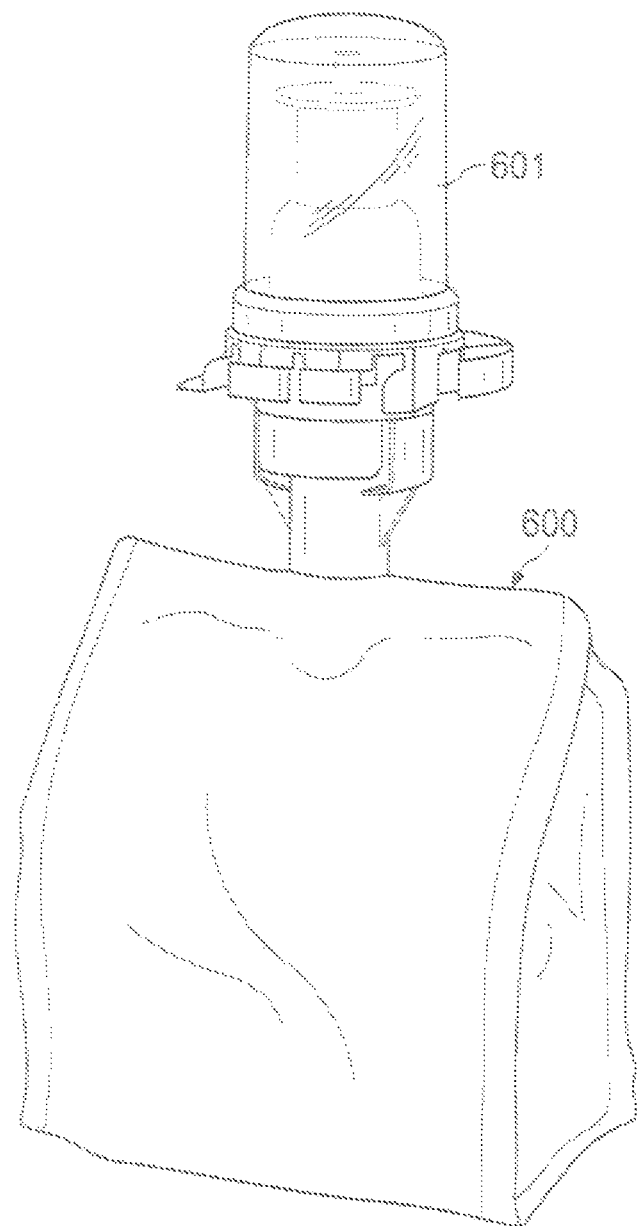
FIG. 6 shows an example of a disposable or refillable bag of sanitizing solution used in one embodiment of the present invention.

Said apparatus further comprises a reservoir which holds a liquid for cleaning or sanitizing, said reservoir comprising an opening leading to said dispensing nozzle via a channel comprising a one-way valve allowing liquid out, and further comprising an opening leading from said positive displacement pump via a channel comprising a one-way valve allowing air in, said reservoir in one embodiment shown in FIG. 6 being a removeable plastic tank or bag 600, said dispensing nozzle and pump openings comprising one-time-use puncturable membranes or lockable valve interfaces 601 corresponding to puncturing mechanisms or complementary locking valve interfaces on said dispensing nozzle and pump openings, respectively. In an embodiment, the reservoir for holding a bag of solution is a thin or narrow form factor so that when it is attached to the interior of the toilet seat lid, it does not significantly extend into the back of the person sitting on the toilet seat, but rather is between ½ and 3 inches in thickness at its apex having a generally oval shape that fits within the confines of the toilet seat when the seat is up or down. In another embodiment, said reservoir may be dimensioned to hold a larger volume of cleaning solution.

Figure 5:
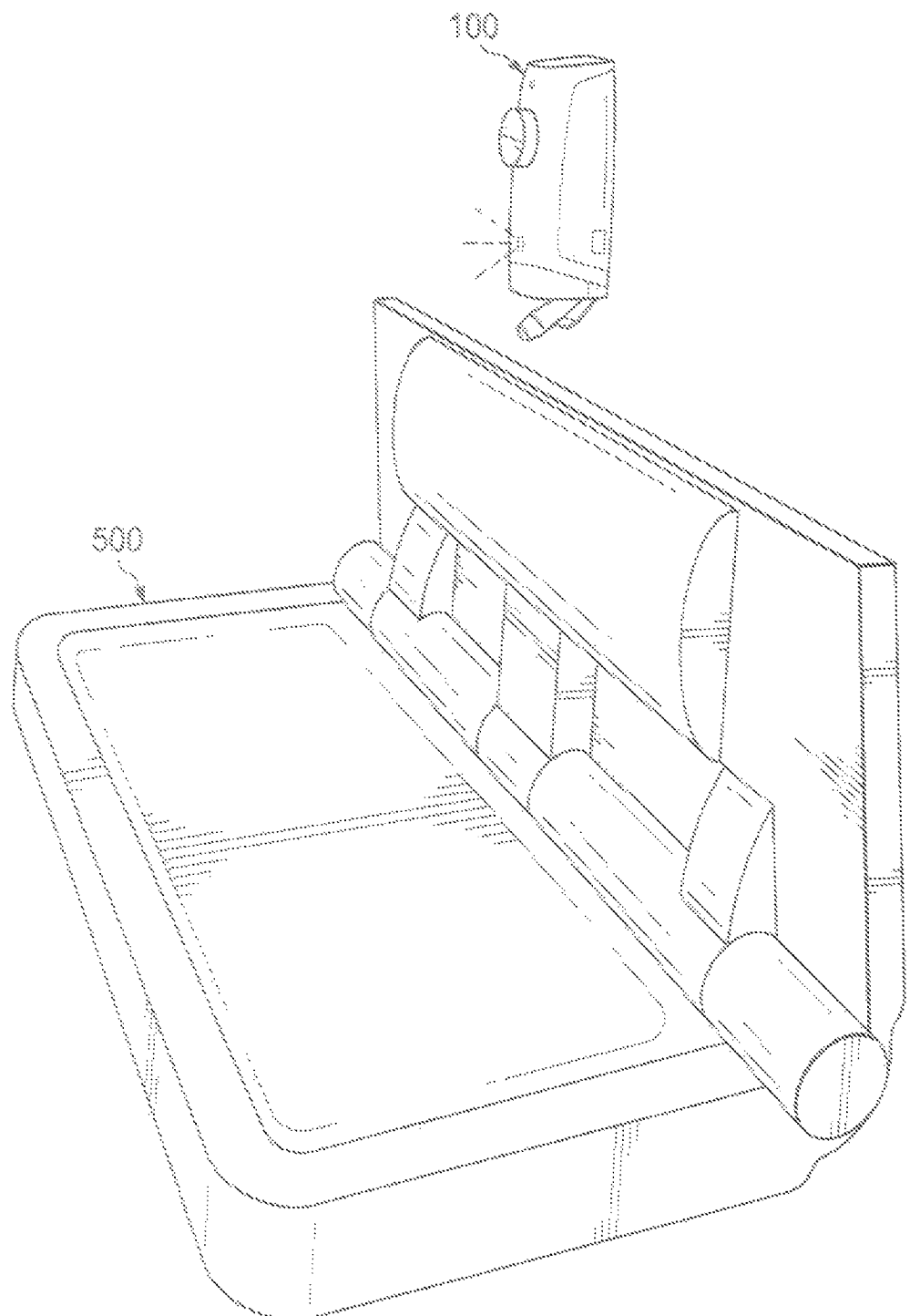
FIG. 5 shows the invention attached to a wall above a baby-changing station in one embodiment of the present invention.

As shown in FIG. 5, the apparatus 100 can be mounted above or nearby any desired surface for sanitization or cleaning purposes, such as sinks, counter tops, baby-changing stations 500, etc. In another embodiment, said apparatus may comprise multiple reservoirs allowing for the dispensing of multiple liquids, oils, or solutions. Said apparatus may, in another embodiment, comprise multiple nozzles tor better coverage of desired surfaces.

In the preferred embodiment the articulated nozzle components (articulation joint, spread adjustment components, nozzle) and reservoir are made of a common plastic such as Polyethylene Terephthalate (PET), Polyvinyl Chloride (PVC), Low Density Polyethylene (LDPE), High Density Polyethylene (HDPE), or Polypropylene (PP).

Figure 7:
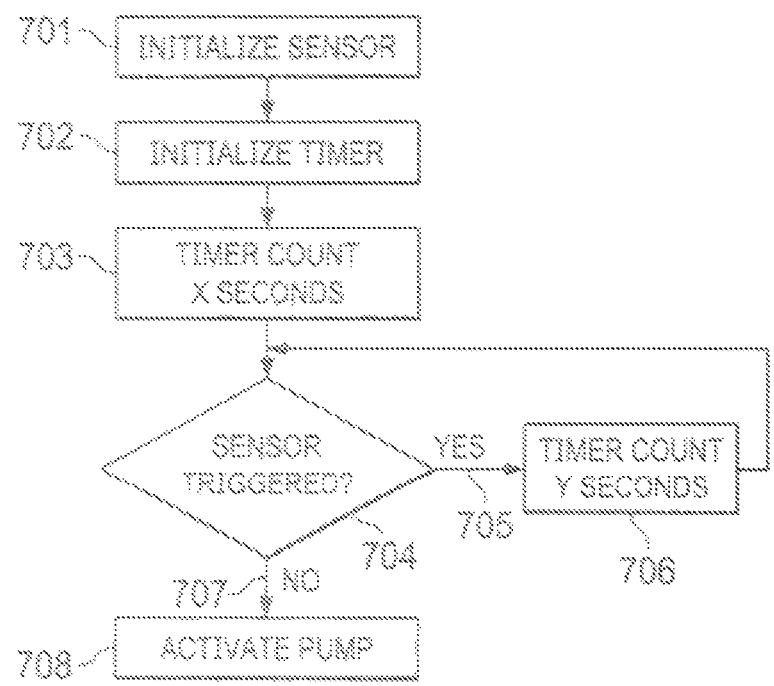
FIG. 7 is a flow chart of a method of activating the pump that dispenses the sanitizing solution.

Referring to FIG. 7, a flow chart of one method of activating the pump with a sensing module so as to dispense the sanitizing fluid such as isopropyl alcohol is provided. In step 701, a touch or touchless sensor is initialized. This may occur when powered on or when batteries are inserted into the sensing module. In step 702, a timer within the module is initialized. The timer then starts a count to X seconds as determined by the user. This might be, for example, 600 seconds, or 10 minutes. When the count is completed, (e.g., 600 seconds have elapsed), then the module notes if the sensor is being triggered in step 704. This can be a proximity sensor for example to determine if someone is near the apparatus. If yes (step 705), then in step 706 the timer counts an additional Y seconds (e.g., 60 seconds or 1 minute) and reverts to step 704 to see it the sensor is triggered. It remains in this loop so long as the sensor is triggered (e.g., someone is near the apparatus). When the sensor is not triggered in step 707, after the timer count completion in step 703, in step 708 the pump is activated, thus dispensing the sanitizing solution.

Once said surface is sufficiently covered or wetted with said solution, a user can then wipe said surface with toilet paper or paper towels which can then be easily disposed in a trashcan or the toilet itself.

Other similar embodiments of the invention include a toilet and toilet bowl sanitizing apparatus having a reservoir for storing cleaning or sanitizing liquid such as isopropyl alcohol or for holding a bag or container of cleaning or sanitizing liquid; a conduit or channel between the reservoir and a dispensing nozzle, wherein the conduit or channel includes a tube connecting the reservoir to the dispensing nozzle for placing the dispensing nozzle in a proximity to the toilet and toilet bowl; the dispensing nozzle coupled to the reservoir via the conduit or channel the dispensing nozzle being any one selected from the group consisting of fixed, telescoping, articulable and hinged, said dispensing nozzle operable to be adjusted to provide a liquid stream of liquid or a flat, round or oval shaped spray of liquid when activated by a pump: the pump operable to pressurize the reservoir or squeeze the bag, forcing solution from said reservoir through a one-way valve and toward said nozzle; a pump activating mechanism; and an attachment mechanism for attaching the apparatus to the toilet.

Further, the pump activating, mechanism is one of a manual push button operable to force cleaning or sanitizing liquid from the reservoir through the dispensing nozzle or a touch or touchless tensor for activating the pump. Further, the pump activating mechanism is a sensor coupled to the pump and when activated by touch or touchless operation, operable to force cleaning or sanitizing liquid from the reservoir or bag through the dispensing nozzle. Further, said reservoir is a vessel for holding a bag of cleaning or sanitizing liquid, said bag being dimensioned to fit within the confines of the reservoir. Further, an opening from said pump activating mechanism through is operable to force air into said bag thus forcing cleaning or sanitizing liquid out of said bag and out the dispensing nozzle. Further, the reservoir is made of a common plastic taken from the group consisting of Polyethylene Terephthalate (PET), Polyvinyl Chloride (PVC), Low Density Polyethylene (LDPE), High Density Polyethylene (HDPE), or Polypropylene (PP).

Further, the dispensing nozzle is an articulation joint such as a ball-and-socket or hinge joint allowing for redirecting of liquid flow; a mechanism for adjusting the spread of liquid leaving said nozzle; and a one-way valve leading from said reservoir allowing liquid to move from said reservoir to said nozzle when acted upon by a pressure differential. Further, the spread adjustment mechanism comprises a screw joint, said screw joint comprising two complementary cylindrical pieces aligned coaxially, one fitting inside the other, the outer surface of said inner piece and the inner surface of said outer piece being threaded such that rotation of one with respect to the other produces relative longitudinal motion of one with respect to the other, said inner piece further is a channel running longitudinally through which liquid travels, said outer piece further is an endcap with openings which acts as a spreader, said pieces dimensioned such that rotation of said outer piece with respect to said inner piece changes the geometry encountered by said liquid and thus changes the spread and behavior of the resulting spray.

Further, said attachment mechanism is an adhesive positional on the rear-facing side of said reservoir. Further, the attachment mechanism is an adjustable mounting bracket having adhesive on an outer rear-facing surface for affixing to a wall, toilet lid, or ceramic tank, said bracket being dimensioned to removably receive said apparatus. Further, the attachment mechanism is a cable or zip ties, said apparatus further having on its rear-facing side an area of high friction material such as rubber, said toilet and toilet bowl sanitizing apparatus being then secured via zip ties to a desired object, with said surface against said object. Further, the activating mechanism is a positive-displacement pump, said pump having a one-way valve between said pump and said reservoir allowing air to enter said reservoir and a push button or mechanical piston operable to force air through said one-way valve into said reservoir.

Further, a blacklight light emitting diode (LED) is coupled to a blacklight LED activation mechanism being a button, touch or touchless sensor, and battery, said blacklight LED being positioned on the same side of said apparatus as said dispensing nozzle such that the area to be cleaned is illuminated by said LED when said LED activation button is pressed or touch or touchless sensor is activated. Said LED is integrated into said apparatus. The apparatus is dimensioned between 8 and 11 inches tall and between 6 and 9 inches wide, such that said apparatus fits into the inner opening of a standard toilet seat.

The invention is further a toilet sanitizing apparatus having an outer shell for holding a disposable bag of cleaning or sanitizing liquid such its isopropyl alcohol, an integrated articulable dispensing nozzle coupled to the outer shell, an attachment mechanism coupled to the outer shell; and a fluid dispensing activation mechanism; said dispensing nozzle comprising an articulation joint such as a ball-and-socket or hinge joint allowing for redirecting of liquid flow from the disposable bag, a spread adjustment mechanism for adjusting the spread of liquid leaving said dispensing nozzle, and a one-way valve leading from said dispensing nozzle allowing liquid to move out from said disposable bag and ejected from said dispensing nozzle when acted upon by an external force such as a pressure differential. Further, the attachment mechanism is one selected from the group consisting of an adhesive positioned on the rear-facing side of said reservoir or apertures dimensioned to accept zip ties to affix the vessel to the toilet or other fixture, an adjustable mounting bracket having adhesive on an outer rear-facing surface for affixing to a walk toilet lid, or ceramic tank, said bracket being dimensioned to removably receive said apparatus, and thin-walled cylindrical brackets positioned along a common axis, being attached to said apparatus along a common longitudinal line, being made of a rigid but flexible material such as a common plastic, and having an opening opposite said attachment line, such that said apparatus may be secured to a pipe or other cylindrical fixture, said brackets opening temporarily via elastic deformation to admit said cylindrical fixture and then returning to their original shape once said fixture is aligned axially with said brackets.

Further the invention has a spread adjustment mechanism being a screw joint, said screw joint comprising two complementary cylindrical pieces aligned coaxially, one fitting inside the other, the outer surface of said inner piece and the inner surface of said outer piece being threaded such that rotation of one with respect to the other produces relative longitudinal motion of one with respect to the other, said inner piece further comprising a channel running longitudinally through which liquid travels, said outer piece further comprising an endcap with openings which acts as a spreader, said pieces dimensioned such that rotation of said outer piece with respect to said inner piece changes the geometry encountered by said liquid and thus changes the spread and behavior of the resulting spray.

Further, the outer shell is dimensioned between 8 and 11 inches tall and between 6 and 9 inches wide, such that said toilet sanitizing apparatus fits into the inner opening of a standard toilet seat and is preferably 9 and ⅞ inches tall and 8 and ¼ inches wide. Further, the outer shell has therewithin a blacklight LED coupled to a blacklight LED activation button and battery, said blacklight LED being positioned on the same side of said apparatus as said dispensing nozzle such that the area to be cleaned is illuminated by said LED when said LED activation button is pressed.

In a further similar embodiment, the invention is a toilet sanitizing apparatus having a reservoir for holding a reservoir for storing cleaning or sanitizing liquid such as isopropyl alcohol, the reservoir having an integrated articulable dispensing nozzle, an attachment mechanism, and an activating mechanism; said dispensing nozzle comprising an articulation joint such as a ball-and-socket or hinge joint allowing for redirecting of liquid flow, a mechanism for adjusting the spread of liquid leaving said nozzle, and a one-way valve leading from said reservoir allowing liquid to move from said reservoir to said nozzle when acted upon by a pressure differential; and a blacklight LED coupled to a blacklight LED activation button and battery, said blacklight LED being positioned on the same side of said apparatus as said dispensing nozzle such that the area to be cleaned is illuminated by said LED when said LED activation button is pressed.

The embodiments shown and described above are only exemplary. Even though numerous characteristics and advantages of the present invention have been set forth in the foregoing description together with details and methods of the present invention, the disclosure is illustrative only and changes may be made within the principles of the invention to the full extent indicated by the broad general meaning of the terms used herein. Various alterations, modifications and substitutions can be made to the details and methods of the disclosed invention without departing in any way from the spirit and scope of the invention.

What is claimed is:

1. A toilet seat sanitizing apparatus comprising:

a reservoir for storing cleaning or sanitizing liquid such as isopropyl alcohol or for holding a bag or container of cleaning or sanitizing liquid;

a conduit or channel between the reservoir and a dispensing nozzle, wherein the conduit or channel includes a tube connecting the reservoir to the dispensing nozzle for placing the dispensing nozzle in a proximity to the toilet and toilet bowl;

the dispensing nozzle coupled to the reservoir via the conduit or channel, the dispensing nozzle being any one selected from the group consisting of articulable and hinged, said dispensing nozzle operable to be adjusted to provide a liquid stream of liquid or a flat, round or oval shaped spray of liquid when activated by a pump;

the pump operable to pressurize the reservoir or squeeze the bag, forcing solution from said reservoir through a one-way valve and toward said nozzle;

a pump activating mechanism; and an attachment mechanism for attaching the apparatus to the toilet;

wherein said dispensing nozzle comprises:

an articulation joint or hinge joint allowing for redirecting of liquid flow;

a mechanism for adjusting the spread of liquid leaving said nozzle; and a one-way valve leading from said reservoir allowing liquid to move from said reservoir to said nozzle when acted upon by a pressure differential;

further wherein said spread adjustment mechanism comprises a screw joint, said screw joint comprising two complementary cylindrical pieces aligned coaxially, one fitting inside the other, the outer surface of said inner piece and the inner surface of said outer piece being threaded such that rotation of one with respect to the other produces relative longitudinal motion of one with respect to the other, said inner piece further comprising a channel running longitudinally through which liquid travels, said outer piece further comprising an endcap with openings which acts as a spreader, said pieces dimensioned such that rotation of said outer piece with respect to said inner piece changes the geometry encountered by said liquid and thus changes the spread and behavior of the resulting spray.

2. The toilet and toilet bowl sanitizing apparatus of claim 1, in which said attachment mechanism comprises an adhesive positioned on the rear-facing side of said reservoir.

3. The toilet and toilet bowl sanitizing apparatus of claim 1, in which said attachment mechanism comprises an adjustable mounting bracket having adhesive on an outer rear-facing surface for affixing to a wall, toilet lid, or ceramic tank, said bracket being dimensioned to removably receive said apparatus.

4. The toilet and toilet bowl sanitizing apparatus of claim 1, in which said attachment mechanism comprises cable or zip ties, said apparatus further comprising on its rear-facing side an area of high-friction material such as rubber, said toilet and toilet bowl sanitizing apparatus being then secured via zip ties to a desired object, with said surface against said object.

5. The toilet and toilet bowl sanitizing apparatus of claim 1, in which said activating mechanism comprises a positive-displacement pump, said pump comprising a one-way valve between said pump and said reservoir allowing air to enter said reservoir and a push button or mechanical piston operable to force air through said one-way valve into said reservoir.

6. The toilet and toilet bowl sanitizing apparatus of claim 1, further comprising a blacklight light emitting diode (LED) coupled to a blacklight LED activation mechanism being a button, touch or touchless sensor, and battery, said blacklight LED being positioned on the same side of said apparatus as said dispensing nozzle such that the area to be cleaned is illuminated by said LED when said LED activation button is pressed or touch or touchless sensor is activated.

7. A toilet seat sanitizing apparatus comprising:

an outer shell for holding a disposable bag of cleaning or sanitizing liquid such as isopropyl alcohol, an integrated articulable dispensing nozzle coupled to the outer shell, an attachment mechanism coupled to the outer shell; and a fluid dispensing activation mechanism;

said dispensing nozzle comprising an articulation joint such as a ball-and-socket or hinge joint allowing for redirecting of liquid flow from the disposable bag, a spread adjustment mechanism for adjusting the spread of liquid leaving said dispensing nozzle, and a one-way valve leading from said dispensing nozzle allowing liquid to move out from said disposable bag and ejected from said dispensing nozzle when acted upon by an external force such as a pressure differential;

said spread adjustment mechanism comprises a screw joint, said screw joint comprising two complementary cylindrical pieces aligned coaxially, one fitting inside the other, the outer surface of said inner piece and the inner surface of said outer piece being threaded such that rotation of one with respect to the other produces relative longitudinal motion of one with respect to the other, said inner piece further comprising a channel running longitudinally through which liquid travels, said outer piece further comprising an endcap with openings which acts as a spreader, said pieces dins one such that rotation of said outer piece with respect to said inner piece changes the geometry encountered by said liquid and thus changes the spread and behavior of the resulting spray.

8. The toilet sanitizing apparatus of claim 7, in which said outer shell is dimensioned between 8 and 11 inches tall and between 6 and 9 inches wide, such that said toilet sanitizing apparatus fits into the inner opening of a standard toilet seat and is preferably 9 and 7/8 inches tall and 8 and 1/4 inches wide.

9. The apparatus of claim 7, in which said outer shell has therewithin a blacklight LED coupled to a blacklight LED activation button and battery, said blacklight LED being positioned on the same side of said apparatus as said dispensing nozzle such that the area to be cleaned is illuminated by said LED when said LED activation button is pressed.

10. A toilet seat sanitizing apparatus comprising:

a reservoir for storing cleaning or sanitizing liquid such as isopropyl alcohol or for holding a bag or container of cleaning or sanitizing liquid;

a conduit or channel between the reservoir and a dispensing nozzle, wherein the conduit or channel includes a tube connecting the reservoir to the dispensing nozzle for placing the dispensing nozzle in a proximity to the toilet and toilet bowl;

the dispensing nozzle coupled to the reservoir via the conduit or channel, the dispensing nozzle being any one selected from the group consisting of articulable and hinged, said dispensing nozzle operable to be adjusted to provide a liquid stream of liquid or a flat, round or oval shaped spray of liquid when activated by a pump;

the pump operable to pressurize the reservoir or squeeze the bag, forcing solution from said reservoir through a one-way valve and toward said nozzle;

a pump activating mechanism; and an attachment mechanism for attaching the entirety of the apparatus to the toilet;

wherein said dispensing nozzle comprises:

an articulation joint or hinge joint allowing for redirecting of liquid flow;

a mechanism for adjusting spread of liquid leaving said nozzle; and a one-way valve leading from said reservoir allowing liquid to move from said reservoir to said nozzle when acted upon by a pressure differential;

said apparatus being positioned and attached to the toilet such that said reservoir or bag, said conduit or channel, said pump, said pump activating mechanism, and said dispensing nozzle are located above the toilet seat and supported in that position by said attachment mechanism.

* * * * *